(12) United States Patent
Auer et al.

(10) Patent No.: US 6,841,700 B2
(45) Date of Patent: Jan. 11, 2005

(54) METHOD FOR PRODUCING ANHYDROUS FORMIC ACID

(75) Inventors: Heinz Auer, Neulussheim (DE); Bernd Bessling, Grosse Ille (DE); Hans Hammer, Mannheim (DE); Hans Hasse, Kaiserslautern (DE); Friedrich Sauer, Obersülzen (DE); Maximilian Vicari, Limburgerhof (DE); Till Adrian, Bobenheim-Roxheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 11 days.

(21) Appl. No.: 10/181,462
(22) PCT Filed: Jan. 12, 2001
(86) PCT No.: PCT/EP01/00344
§ 371 (c)(1), (2), (4) Date: Jul. 18, 2002
(87) PCT Pub. No.: WO01/53244
PCT Pub. Date: Jul. 26, 2001

(65) Prior Publication Data
US 2003/0018216 A1 Jan. 23, 2003

(30) Foreign Application Priority Data
Jan. 24, 2000 (DE) .......................................... 100 02 791

(51) Int. Cl.$^7$ .............................................. C07C 53/02
(52) U.S. Cl. ....................................... 562/609; 562/606
(58) Field of Search .................................. 562/512, 609; 560/129

(56) References Cited

U.S. PATENT DOCUMENTS
3,983,010 A * 9/1976 Rauch et al. .................. 203/15
4,326,073 A * 4/1982 Wolf et al. ................... 562/609

FOREIGN PATENT DOCUMENTS
| | | |
|---|---|---|
| DE | 34 28 319 | 2/1986 |
| EP | 0 017 866 | 10/1980 |
| EP | 0 596 484 | 5/1994 |

OTHER PUBLICATIONS
Ullmanns Encyklopädie der technischen Chemie 4th Ed. vol. 7, pp. 365–366.

* cited by examiner

Primary Examiner—Johann Richter
Assistant Examiner—Karl J. Puttlitz
(74) Attorney, Agent, or Firm—Keil & Weinkauf

(57) ABSTRACT

The invention relates to a process for obtaining anhydrous or substantially anhydrous formic acid, in which firstly aqueous formic acid is produced by hydrolysis of methyl formate, with the methanol content in the methyl formate having been reduced in advance. The process according to the invention has the special feature that—before the hydrolysis of the methyl formate—the methanol content of the methanol-containing methyl formate is reduced in a distillation column, this distillation column simultaneously being employed for other separation functions during work-up of the formic acid.

6 Claims, 4 Drawing Sheets

METHOD FOR PRODUCING ANHYDROUS FORMIC ACID

Figure 1:
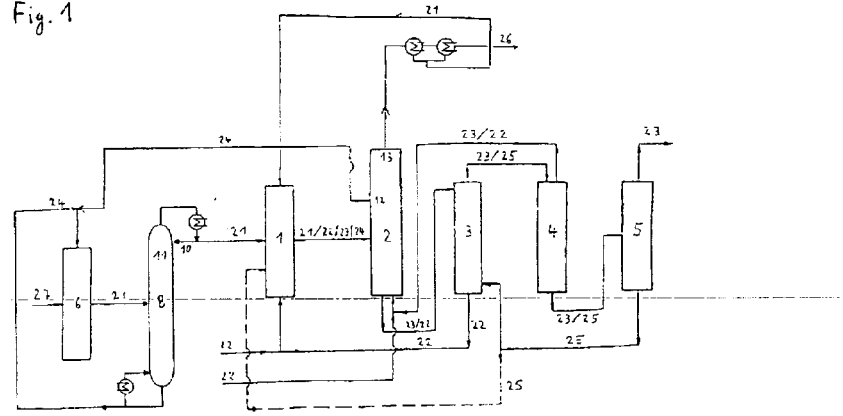

The present invention relates to a process and an apparatus for obtaining anhydrous or substantially anhydrous formic acid.

"Ullmanns Encyklopädie der technischen Chemie" [Ullmann's Encyclopedia of Industrial Chemistry], 4$^{th}$ Edition, Volume 7, page 365, discloses that formic acid can be prepared by acidolysis of formamide using sulfuric acid. However, this process has the disadvantage that stoichiometric amounts of ammonium sulfate are obtained as an unavoidable product.

Another way of preparing formic acid consists in the hydrolysis of methyl formate, which is synthesized from methanol and carbon monoxide. This synthesis is based on the following equations:

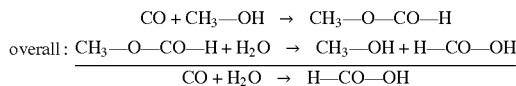

The hydrolysis of methyl formate described in "Ullmanns Encyklopädie der technischen Chemie" [Ullmann's Encyclopedia of Industrial Chemistry], 4$^{th}$ Edition, Volume 7, page 366

has the disadvantage of an unfavorable position of the hydrolysis equilibrium. A shift in the equilibrium by removing the desired process products by distillation is not possible since methyl formate (boiling point 32° C.) boils significantly lower than methanol (boiling point 65° C.) and formic acid (boiling point 101° C.). Anhydrous formic acid cannot easily be obtained from the resultant aqueous formic acid solution by distillation since it forms an azeotrope with water. The difficulty thus consists in obtaining anhydrous formic acid from the methyl formate hydrolysis mixture.

A process described in EP-B-0 017 866 which comprises the important steps a) to g) enables the preparation of anhydrous formic acid starting from methyl formate. Anhydrous formic acid is obtained here if a) methyl formate is subjected to hydrolysis, b) methanol and excess methyl formate are distilled off from the resultant hydrolysis mixture, c) the bottom product from the distillation (b), which comprises formic acid and water, is extracted in a liquid-liquid extraction with an extractant which principally takes up the formic acid, d) the resultant extract phase, comprising formic acid, extractant and some of the water, is subjected to distillation, e) the top product obtained in this distillation, which comprises water and some of the formic acid, is fed back into the lower part of the distillation column in step (b), f) the bottom product from distillation step (d), which comprises predominantly extractant and formic acid, is separated by distillation into anhydrous formic acid and the extractant, and g) the extractant leaving step (f) is fed back into the process.

In this process, it is particularly advantageous h) to carry out distillation steps (b) and (d) in a single column, i) to introduce the water necessary for the hydrolysis in the form of steam into the lower part of the column provided for carrying out step (b), k) to employ methyl formate and water in the hydrolysis (a) in a molar ratio of from 1:2 to 1:10, and/or l) to employ, as extractant, a carboxamide of the general formula I

where the radicals R$^1$ and R$^2$ are alkyl, cycloalkyl, aryl or aralkyl groups, or R$^1$ and R$^2$ jointly, together with the N atom, form a heterocyclic 5- or 6-membered ring, and only one of the radicals is an aryl group, and where R$^3$ is hydrogen or a C$_1$–C$_4$-alkyl group.

Steps (a) to (i) are explained in greater detail below.

Step (a)

The hydrolysis is usually carried out at a temperature in the range from 80 to 150° C.

Step (b)

The distillation of the hydrolysis mixture can in principle be carried out at any desired pressure, preferably from 0.5 to 2 bar. In general, working under atmospheric pressure is advisable. In this case, the temperature at the bottom of the column is about 110° C. and the temperature at the top of the column is from about 30 to 40° C. The hydrolysis mixture is advantageously added at a temperature in the range from 80 to 150° C., and the methanol is preferably removed in liquid form at a temperature of from 55 to 65° C. Satisfactory separation of the mixture into methyl formate and methanol on the one hand and aqueous formic acid on the other hand is possible even using a distillation column which has 25 theoretical plates (the theoretical number of plates is preferably from 35 to 45). Any design can be used for the column intended for step (b), but a sieve-plate or packed column is particularly recommended.

Step (c)

The liquid-liquid extraction of the formic acid from its aqueous solution by means of an extractant is preferably carried out at atmospheric pressure and a temperature of from 60 to 120° C., in particular from 70 to 90° C., in countercurrent. Depending on the type of extractant, extraction devices having from 1 to 12 theoretical separation stages are generally required. Suitable extraction devices for this purpose are in particular liquid-liquid extraction columns. In most cases, satisfactory results are achieved using from 4 to 6 theoretical separation stages.

The choice of extractant is not limited. Particularly suitable extractants are carboxamides of the general formula I given above. Extractants of this type are, in particular, N,N-di-n-butylformamide and in addition N,N-di-n-butylacetamide, N-methyl-N-2-heptylformamide, N-n-butyl-N-2-ethylhexylformamide, N-n-butyl-N-cyclohexylformamide and N-ethylformanilide, and mixtures of these compounds. Further suitable extractants are, inter alia, diisopropyl ether, methyl isobutyl ketone, ethyl acetate, tributyl phosphate and butanediol formate.

Step (d)

The extract phase is separated by distillation in an appropriate distillation device into a liquid phase, which generally comprises predominantly formic acid and extractant, and a vapor phase predominantly comprising water and small amounts of formic acid. This is an extractive distillation. The bottom temperature is preferably from 140 to 180° C. A satisfactory separation effect is generally achieved from 5 theoretical plates.

Step (e)

The formic acid/water mixture is generally recycled in vapor form.

Steps (f) and (g)

The distillation device (usually in the form of a column) for carrying out step (f) is advantageously operated under reduced pressure—from about 50 to 300 mbar and correspondingly low head temperatures—from about 30 to 60° C.

Step (h)

This variant of the process relates to steps (b) and (d). The distillation devices for carrying out steps (b) and (d) are arranged in an overall distillation device. The distillation devices here are generally in the form of columns.

Step (i)

In this step, water required for the hydrolysis is provided in the form of steam.

The industrial synthesis of methyl formate from carbon monoxide and methanol is carried out using a molar excess of methanol. The reactor discharge from the corresponding synthesis reactor therefore, therefore, in addition to methyl formate, still contains considerable quantities of excess methanol. The reactor discharge usually contains from 20 to 40% by weight of methanol—the remainder consisting essentially of methyl formate. The economic efficiency of the process described in EP-B-0 017 866 is improved by reducing the content of methanol in the mixture of methyl formate and methanol taken from the synthesis reactor and only then feeding the mixture to the hydrolysis reactor for carrying out step a). The most economical procedure is to introduce a methyl formate stream comprising about 95% of methyl formate into the hydrolysis reactor—the methanol content in this stream is accordingly significantly lower than in the stream leaving the synthesis reactor. The reduction in the methanol content is carried out in a distillation column fitted with a rectifying section and having a return at the top. The evaporation enthalpy of the return in this column must be introduced in the still evaporator in the form of steam, i.e. additional energy must be introduced into the process. Besides this disadvantage of high energy costs, the economic efficiency of the process is also adversely affected by the high investment costs for the corresponding column. The costs for the provision of methyl formate containing only small quantities of methanol (for example 5% by weight) thus reduces the economic advantage arising from the use of highly concentrated methyl formate.

It is an object of the present invention to provide a process in which anhydrous or substantially anhydrous formic acid is obtained. The aim is to improve the economic efficiency of the process in such a way that expenditure on energy and equipment for reducing the content of methanol in the mixture of methyl formate and methanol employed for the hydrolysis is reduced.

We have found that this object is achieved by a process for obtaining anhydrous or substantially anhydrous formic acid in which i) methyl formate is subjected to hydrolysis,
ii) methanol and excess methyl formate are distilled off from the resultant hydrolysis mixture,
iii) the bottom product from distillation ii), comprising formic acid and water, is extracted in a liquid-liquid extraction with an extractant which principally takes up the formic acid,
iv) the resultant extract phase, comprising formic acid, extractant and some of the water, is subjected to distillation,
v) the top product obtained in this distillation, which comprises water and some of the formic acid, is fed back into the lower part of the distillation device in step ii),
vi) the bottom product from distillation step iv), which comprises predominantly extractant and formic acid, is separated by distillation into anhydrous or substantially anhydrous formic acid and the extractant, and
vii) the extractant leaving step vi) is fed back into the process, which comprises feeding methanol-containing methyl formate into the distillation device proposed for carrying out step ii) before the hydrolysis of the methyl formate (step i)), where the corresponding feed point for the methanol-containing methyl formate in the distillation device is located above the removal point for methanol and below the removal point for methyl formate, and methyl formate with a reduced methanol content is obtained at the removal point for methyl formate and is subsequently fed to step i).

The term "substantially anhydrous formic acid" is taken to mean formic acid which comprises up to a maximum of 30% by weight, preferably up to a maximum of 15% by weight, of water. The term "methyl formate with a reduced methanol content" is taken to mean methyl formate which contains less methanol than the methyl formate leaving the synthesis reactor.

An essential advantage is that methyl formate having a higher content of methanol (for example 30%) can also be provided for the process according to the invention. This results in a reduction in expenditure on energy and equipment, and the process can thus be operated more economically. An essential advantage is thus that a simple distillation column in the form of a stripping column (without rectifying section and return) is sufficient for concentrating the methyl formate from the synthesis reactor if the partially concentrated methyl formate stream obtained in this way is fed into the distillation device ii), where it can be concentrated to the desired 95%, for example, without additional energy expenditure.

In a preferred embodiment of the invention, the methanol-containing methyl formate is obtained by feeding the mixture of methyl formate and methanol removed from the synthesis reactor to a distillation column, preferably in the form of a stripping column, removing some of the methanol therein, and removing the methanol-containing methyl formate at the upper end of the distillation column. In general, the distillation column, preferably in the form of a stripping column, has no rectifying section. There is preferably no return in the upper section of the distillation column. A distillation column of this type is able to reduce the methanol content in the methyl formate, which is subsequently fed to the distillation device for carrying out step ii), to a sufficient extent. A particular advantage of a distillation column of this type is the lower construction costs, which can be minimized, in particular, through the omission of a rectifying section and a return. Due to the reduction in the amount of heating steam, the size of the column's heat exchangers and the cooling water needed by the corresponding condenser can also be reduced.

Distillation steps ii) and iv) are advantageously carried out in a single distillation device. This correspondingly carries out the functions of the individual distillation columns. The water needed for the hydrolysis (step i)) is preferably fed in the form of steam to the lower part of the distillation device proposed for carrying out step ii).

An apparatus for carrying out the process described above is also provided in accordance with the invention. This comprises α) a synthesis reactor,
β) a hydrolysis reactor,
χ) a distillation device for carrying out step ii), having a feed point for methanol-containing methyl formate and removal points for methanol and methyl formate, δ) a distillation device for carrying out step iv), ε) an extraction device, and φ) a distillation device for carrying out step vi).

Suitable synthesis reactors are all reactors which are suitable for the preparation of methyl formate starting from methanol and carbon monoxide. The distillation devices χ), δ) and φ are generally in the form of columns. The extraction device employed is preferably a liquid-liquid extraction column.

In a preferred embodiment, the apparatus according to the invention also comprises, besides elements α) to φ), a distillation column, which is preferably in the form of a stripping column, i.e. has neither a rectifying section in the upper part nor is provided with a return. The distillation column preferably in the form of a stripping column serves for the removal of excess methanol from the reaction mixture in the synthesis reactor.

The distillation device for carrying out step ii) and the distillation device for carrying out step iv) are preferably arranged in a single distillation device. The latter is usually in the form of a large column having the distillation device for carrying out step ii) in the upper part and the distillation device for carrying out step iv) in the lower part.

Figure 2:
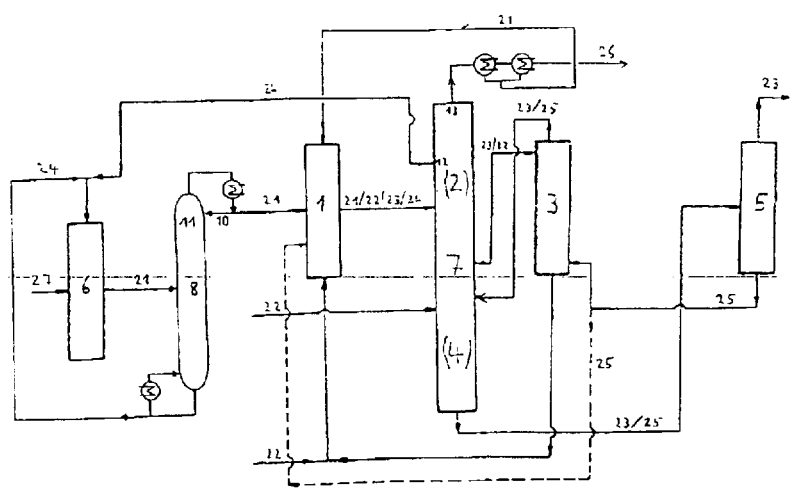
Figure 3:
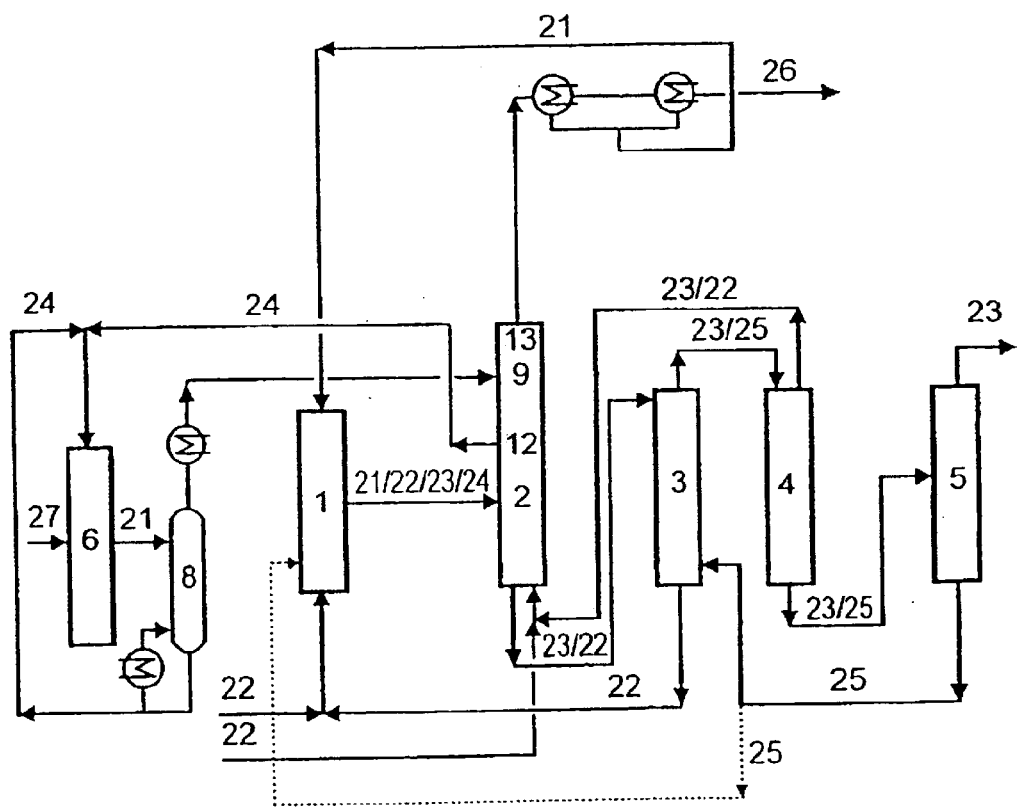
Figure 4:
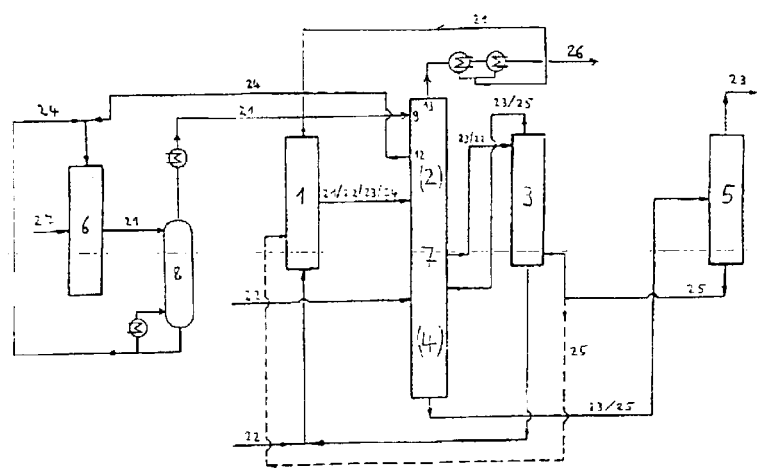

The drawing shows in FIG. 1 a diagram of a plant for the preparation of anhydrous or substantially anhydrous formic acid in accordance with the prior art, in FIG. 2 a diagram of a plant for the preparation of anhydrous or substantially anhydrous formic acid in accordance with the prior art, where the distillation device for carrying out step ii) and the distillation device for carrying out step iv) are arranged in a single distillation device, in FIG. 3 a diagram of a plant for carrying out the process according to the invention for the preparation of anhydrous or substantially anhydrous formic acid, and in FIG. 4 a diagram of a plant for carrying out the process according to the invention for the preparation of anhydrous or substantially anhydrous formic acid in which the distillation device for carrying out step ii) and the distillation device for carrying out step iv) are arranged in a single distillation device.

The reference numerals entered above or alongside the arrows indicate the components which generally have a high content or the principal content in the respective streams. Since the proportions of the components in the streams may vary, these reference numerals should only serve as guide values for information. Reference numeral 21 denotes methyl formate, 22 denotes water, 23 denotes formic acid, 24 denotes methanol, 25 denotes extractants, 26 denotes offgas and 27 denotes carbon monoxide. It is common to the prior-art process and the process according to the invention that methyl formate is prepared in a synthesis reactor 6, the hydrolysis of the methyl formate is carried out in a hydrolysis reactor 1, and step ii) is carried out in the distillation device 2, the extraction is carried out in an extraction device 3, step iv) is carried out in a distillation device 4, and step vi) is carried out in a distillation device 5.

In FIG. 2 and FIG. 4, the distillation devices 2; 4 are arranged in a single distillation device 7. The processes according to the invention and the prior-art processes differ in that the methyl formate- and methanol-containing stream discharged from the synthesis reactor is fed to distillation columns 8 with different designs. The distillation columns in accordance with the prior art contain a rectifying section 11 and a return 10—these elements are not present in the plants for the process according to the invention. The methyl formate containing a residual amount of methanol leaving the distillation column 8 is, in the prior-art process, fed directly into the hydrolysis reactor 1. By contrast, the methanol-containing methyl formate leaving the distillation column 8 is, in the process according to the invention, fed to the distillation device 2, the corresponding feed point 9 being arranged above the removal point for methanol 12 and below the removal point for methyl formate 13. The methyl formate obtained at the removal point 13 for methyl formate has had its methanol content reduced in the distillation device 2. This methyl formate with a reduced methanol content is then fed to the hydrolysis reactor 1.

The invention will be explained in greater detail below with reference to a working example.

COMPARATIVE EXAMPLE

The comparative example corresponds to a process in accordance with the prior art which is carried out in a plant shown diagrammatically in FIG. 1. 5.3 kg of aqueous formic acid are prepared. The mixture of methyl formate and methanol leaving the synthesis reactor 6 is fed into the distillation column 8 containing the rectifying section 11, methyl formate being concentrated to 95% by weight in this column.

The latter is fed into the hydrolysis reactor 1. The reaction product from the synthesis reactor contains 25% by weight of methanol in addition to the methyl formate. The distillation column 8 having the rectifying section 11 is in the form of a bubble-cap plate, with a total of 30 plates. The mixture removed from the synthesis reactor 6 is introduced onto plate 15. The bubble-cap plate column contains a still evaporator which supplies 0.9 kW of heat, and a head condenser which withdraws 0.95 kW of heat. The distillation device 2 is in the form of a glass bubble-cap column with 80 plates. The feed of the mixture removed from the hydrolysis reactor 1 takes place onto plate 15. In addition, the condensed, liquid head stream from the distillation device 4 is introduced into the still of the distillation device 2. Liquid methanol for recirculation into the methyl formate synthesis is taken off at the removal point 12—the removal point 12 is located at plate 50. 95% by weight methyl formate is taken off at the removal point 13 at the top of the distillation device 2. To this end, 4.9 kW of heat must be supplied in the still evaporator of the corresponding distillation device 7. 4.5 kW of heat are withdrawn at the head condenser.

EXAMPLE

The following illustrative experiment corresponds to a process according to the invention carried out in a plant shown diagrammatically in FIG. 3. As in the above prior-art process, 5.3 kg of aqueous formic acid are prepared. The reaction product from synthesis reactor 6 contains 25% by weight of methanol in addition to methyl formate. The concentration of the methyl formate is carried out in a distillation column 8 in the form of a "pure" stripping column which has only 15 plates. The mixture removed from the synthesis reactor is introduced onto the uppermost plate, and consequently the column has no rectifying section 11. 0.6 kW of heat—33% less than in the corresponding prior-art process—is introduced into the still evaporator of the distillation column 8, and 0.73 kW –23% less than in the prior-art process—of heat is withdrawn at the corresponding condenser (the saving of cooling water is associated therewith). With the aid of this apparatus arrangement, methyl formate is concentrated to 89% by weight. The resultant stream is introduced into the distillation device 2 at the feed point 9. The distillation device 2 differs with respect to the one employed in the comparative experiment only through the feed point 9. This is located at plate 65. The energy introduced by the still evaporator of the distillation device 7 corresponds to that in the comparative experiment. The methyl formate concentration at the removal point 13 is 95% by weight.

The distillation column 8 in the form of a "pure" stripping column has only half the physical height compared with the distillation column 8 employed in the comparative experiment. Owing to the low energy introduction necessary, the heat exchangers (evaporator/condenser) can be 30% smaller. The column diameter can be reduced by 10%.

It can clearly be seen that the process according to the invention is significantly improved over the prior-art process with respect to energy and investment costs.

We claim:

1. A process for obtaining anhydrous or substantially anhydrous formic acid, in which
    i) methyl formate is subjected to hydrolysis,
    ii) methanol and excess methyl formate are distilled off from the resultant hydrolysis mixture,
    iii) the bottom product from distillation ii), which comprises formic acid and water, is extracted in a liquid—liquid extraction with an extractant which principally takes up the formic acid,
    iv) the resultant extract phase, comprising formic acid, extractant and some of the water, is subjected to distillation,
    v) the top product obtained in this distillation, which comprises water and some of the formic acid, is fed back into the lower part of the distillation device in step ii),
    vi) the bottom product from distillation step iv), which comprises predominantly extractant and formic acid, is separated by distillation into anhydrous or substantially anhydrous formic acid and the extractant, and
    vii) the extractant leaving step vi) is fed back into the process, which comprises feeding methanol-containing methyl formate into the distillation device for carrying out step ii) before the hydrolysis of the methyl formate (step i)), where the corresponding feed point for the methanol-containing methyl formate in the distillation device is located above the removal point for methanol an below the removal point for methyl formate, and methyl format with a reduced methanol content is obtained at the removal point for methyl formate and is subsequently fed to step i).

2. The process as claimed in claim 1, wherein the methanol-containing methyl formate is obtained by feeding the mixture of methyl formate and methanol removed from the synthesis reactor to a distillation column, separating off some of the methanol therein, and removing the methanol-containing methyl formate at the upper end of the distillation column.

3. The process as claimed in claim 2, wherein the distillation column has no rectifying section.

4. The process as claimed in claim 2, wherein the distillation column has no return in the upper section.

5. The process as claimed in claim 1, wherein distillation steps ii) and iv) are carried out in single distillation device.

6. The process as claimed in claim 2, wherein the distillation column to which the mixture of methyl formate and methanol removed from the synthesis reactor is fed is a stripping column.

* * * * *